(12) United States Patent
Cohn

(10) Patent No.: US 8,715,194 B2
(45) Date of Patent: May 6, 2014

(54) SCREENING FOR EARLY DETECTION OF CARDIOVASCULAR DISEASE IN ASYMPTOMATIC INDIVIDUALS

(75) Inventor: Jay N. Cohn, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 1207 days.

(21) Appl. No.: 11/545,812

(22) Filed: Oct. 10, 2006

(65) Prior Publication Data

US 2007/0060821 A1    Mar. 15, 2007

Related U.S. Application Data

(63) Continuation of application No. 10/372,001, filed on Feb. 21, 2003, now abandoned.

(60) Provisional application No. 60/359,117, filed on Feb. 21, 2002.

(51) Int. Cl.
*A61B 5/02* (2006.01)

(52) U.S. Cl.
USPC ............................ 600/481; 600/485; 600/509

(58) Field of Classification Search
USPC .......................................... 600/481, 485, 509
See application file for complete search history.

(56) References Cited

U.S. PATENT DOCUMENTS

| | | | |
|---|---|---|---|
| 5,054,493 A * | 10/1991 | Cohn et al. ................... | 600/485 |
| 5,396,886 A | 3/1995 | Cuypers | |
| 6,110,109 A * | 8/2000 | Hu et al. ....................... | 600/300 |
| 6,322,504 B1 * | 11/2001 | Kirshner ....................... | 600/300 |
| 6,331,161 B1 * | 12/2001 | Chesney et al. ............... | 600/485 |
| 2004/0260185 A1 * | 12/2004 | Anderson et al. ............. | 600/481 |

OTHER PUBLICATIONS

D. Gareth Beevers et al., Hypertension in Practice, 1999, Informa Health Care.*
Anonymous, "Effect of enalapril on mortality and the development of heart failure in asymptomatic patients with reduced left ventricular ejection fractions. The SOLVD Investigators", *New England Journal of Medicine*, 327(10), (Sep. 3, 1992),685-91.
Anonymous, "Prevention of cardiovascular events and death with pravastatin in patients with coronary heart disease and a broad range of initial cholesterol levels. The Long-Term Intervention with Pravastatin in Ischaemic Disease (LIPID) Study Group", *New England Journal of Medicine*, 339(19), (Nov. 5, 1998), 1349-57.
Anonymous, "Randomised trial of cholesterol lowering in 4444 patients with coronary heart disease: the Scandinavian Simvastatin Survival Study", *Lancet*, 344(8934), (Nov. 19, 1994),1383-9.

(Continued)

*Primary Examiner* — Joseph Stoklosa
(74) *Attorney, Agent, or Firm* — Schwegman Lundberg & Woessner, P.A.

(57) ABSTRACT

Screening apparently healthy individuals using sensitive techniques for identifying early vascular and cardiac disease provides the opportunity for effective intervention to prevent or delay the occurrence of cardiovascular events which represent the most common cause of morbidity and mortality in our society. Preliminary studies have revealed an incidence of over 50% of early disease in need of therapy. The apparent ineffectiveness of the health care system to uncover this early disease emphasizes the need for a more aggressive community approach to screen for early disease and to initiate therapy that should reduce health care costs and improve quality and duration of life.

6 Claims, 6 Drawing Sheets

| Test | Normal | Borderline | Abnormal |
|---|---|---|---|
| Arterial Elasticity | See Figure 1 | | |
| Resting blood pressure (mmHg) | SBP<130 and DBP <85 | SBP 130-139 or DBP 85-89 | SBP≥140 Or DBP≥90 |
| Exercise blood pressure (mmHg) | SBP rise <30 and SBP ≤169 | SBP rise 30-39 or SBP 170-179 | SBP rise ≥40 or SBP ≥180 |
| Optic fundus | A:V ratio >3:5 | A:V ratio ≤3:5 or Mild A:V crossing changes | A:V ratio ≤1:2 or A:V nicking |
| Microalbuminuria (mg/mmol) | ≤0.6 | 0.61-0.99 | ≥1.00 |
| Ankle-brachial index | >0.90 | -- | <0.90 |
| Electrocardiogram | No abnormalities | Non-Specific Abnormality | Diagnostic abnormality |
| LV Ultrasound | LVIDD/BSA <2.70 cm And LVM/BSA <120 gm | 2.70-2.89 cm or 120-129 gm | ≥2.9 cm or ≥130 gm |
| BNP (pg/dl) | ≤50 | 51-99 | ≥100 |

(56) References Cited

OTHER PUBLICATIONS

Anonymous, "Secondary prevention of vascular disease by prolonged antiplatelet treatment. Antiplatelet Trialists' Collaboration", *British Medical Journal*, 296(6618), (Jan. 30, 1988),320-31.

Borch-Johnsen, K, et al., "Urinary albumin excretion. An independent predictor of ischemic heart disease", *Arteriosclerosis, Thrombosis & Vascular Biology*, 19(8), (Aug. 1999), 1992-7.

Clarke, R, et al., "Hyperhomocysteinemia: an independent risk factor for vascular disease", *New England Journal of Medicine*, 324(17), (Apr. 25, 1991), 1149-55.

Cohn, J N., "Arteries, myocardium, blood pressure and cardiovascular risk: towards a revised definition of hypertension", *Journal of Hypertension*, 16(12 Pt 2), (Dec. 1998), 2117-24.

Cohn, J. N., "Noninvasive pulse wave analysis for the early detection of vascular disease", *Hypertension*, 26(3), (Sep. 1995),503-508.

Downs, S L., et al., "Primary prevention of acute coronary events with lovastatin in men and women with average cholesterol levels: results of AFCAPS/TexCAPS. Air Force/Texas Coronary Atherosclerosis Prevention Study", *JAMA*, 279(20), (May 27, 1998),1615-22.

Gottlieb, S S., et al., "Effect of beta-blockade on mortality amonghigh-risk and low-risk patients after myocardial infarction", *New England Journal of Medicine*, 339(8), (Aug. 20, 1998),489-97.

Grundy, S M., et al., "Primary prevention of coronary heart disease: guidance from Framingham: a statement for healthcare professionals from the AHA Task Force on Risk Reduction. American Heart Association", *Circulation*, 97(18), (May 12, 1998),1876-87.

Hirsch, A T., et al., "Peripheral arterial disease detection, awareness, and treatment in primary care", *JAMA*, 286(11), (Sep. 19, 2001),1317-24.

Kannel, William B., "Blood pressure as a cardiovascular risk factor: prevention and treatment", *JAMA*, 275(20), (May 22-29, 1996),1571-6.

Lim, P , et al., "Dundee step test: a simple method of measuring the blood pressure response to exercise", *Journal of Human Hypertension*, 13(8), (Aug. 1999),521-6.

Maisel, A S., "Utility of B-natriuretic peptide as a rapid, point-of-care test for screening patients undergoing echocardiography to determine left ventricular dysfunction", *American Heart Journal*, 141(3), (Mar. 2001),367-74.

Merit-HF Study Group, "Effect of metoprolol CR/XL in chronic heart failure: Metoprolol CR/XL Randomised Intervention Trial in Congestive Heart Failure (MERIT-HF)", *Lancet*, 353(9169), (Jun. 12, 1999),2001-7.

Ridker, P M., et al., "C-reactive protein adds to the predictive value of total and HDL cholesterol in determining risk of first myocardial infarction", *Circulation*, 97(20), (May 26, 1998),2007-11.

Ross, R , "The pathogenesis of atherosclerosis: a perspective for the 1990s", *Nature*, 362(6423), (Apr. 29, 1993),801-9.

Stein, J H., et al., "Lipoprotein Lp(a) excess and coronary heart disease", *Archives of Internal Medicine*, 157(11), (Jun. 9, 1997),1170-6.

Yusuf, S , et al., "Effects of an angiotensin-converting-enzyme inhibitor, ramipril, on cardiovascular events in high-risk patients. The Heart Outcomes Prevention Evaluation Study Investigators", *New England Journal of Medicine*, 342(3), (Jan. 20, 2000),145-53.

\* cited by examiner

Figure 1

| Age Category (years) | Gender | C1 (capacitive)(ml/mmHgx10) | | | C2 (oscillatory)(ml/mmHgx100) | | |
|---|---|---|---|---|---|---|---|
| | | Normal | Borderline | Abnormal | Normal | Borderline | Abnormal |
| ≤45 | Male | ≥15 | 12-14.9 | <12 | ≥7 | 6-6.9 | <6 |
| | Female | | | | ≥5 | 4-4.9 | <4 |
| 46-64 | Male | ≥12 | 10-11.9 | <10 | ≥6 | 5-5.9 | <5 |
| | Female | | | | ≥4 | 3.5-3.9 | <3.5 |
| ≥65 | Male | ≥10 | 8-9.9 | <8 | ≥5 | 4-4.9 | <4 |
| | Female | | | | ≥3 | 2.5-2.9 | <2.5 |

Figure 2

| Test | Normal | Borderline | Abnormal |
|---|---|---|---|
| Arterial Elasticity | See Figure 1 | | |
| Resting blood pressure (mmHg) | SBP<130 and DBP <85 | SBP 130-139 or DBP 85-89 | SBP≥140 Or DBP≥90 |
| Exercise blood pressure (mmHg) | SBP rise <30 and SBP ≤169 | SBP rise 30-39 or SBP 170-179 | SBP rise ≥40 or SBP ≥180 |
| Optic fundus | A:V ratio >3:5 | A:V ratio ≤3:5 or Mild A:V crossing changes | A:V ratio ≤1:2 or A:V nicking |
| Microalbuminuria (mg/mmol) | ≤0.6 | 0.61-0.99 | ≥1.00 |
| Ankle-brachial index | >0.90 | -- | <0.90 |
| Electrocardiogram | No abnormalities | Non-Specific Abnormality | Diagnostic abnormality |
| LV Ultrasound | LVIDD/BSA <2.70 cm And LVM/BSA <120 gm | 2.70-2.89 cm or 120-129 gm | ≥2.9 cm or >130 gm |
| BNP (pg/dl) | ≤50 | 51-99 | ≥100 |

Figure 3

| | Laboratory Test | Reference Range | | | Units |
|---|---|---|---|---|---|
| | | Optimal | Borderline | Abnormal | |
| HDL-C | HDL Cholesterol | ≥45 men<br>≥55 women | 40-45 men<br>50-55 women | ≤40 men<br>≤50 women | mg/dL |
| LDL-C | LDL Cholesterol | ≤100 | 101-129 | ≥130 | mg/dL |
| TG | Triglycerides | ≤150 | 151-199 | ≥200 | mg/dL |
| GLUC | Glucose | ≤110 | 111-125 | ≥126 | mg/dL |
| HsCRP | C-Reactive Protein | ≤0.300 | | >0.300 | mg/dL |
| PAI-1 | Plasminogen Activator Inhibitor-1 | ≤43 | | >43 | ng/dL |
| HCY | Homocysteine | ≤10 | 10.1-12 | >12 | μmo/L |

Figure 4

| Age Category | Gender | |
|---|---|---|
| | Male | Female |
| Age 24 and under | 0 (0%) | 2 (0.6%) |
| Age 25-34 | 15 (4.5%) | 10 (3%) |
| Age 35-44 | 60 (18%) | 23 (7%) |
| Age 45-54 | 56 (17%) | 34 (10%) |
| Age 55-64 | 51 (15%) | 31 (9%) |
| Age 65-74 | 24 (7%) | 19 (6%) |
| Age 75 and over | 5 (1.5%) | 3 (1%) |
| Total by gender | 211 (63%) | 122 (36%) |

Figure 5

| Age Category | Gender | Pulse Wave* | | | Resting BP | | | Exercise BP | | | Retinal Photoexam | | | ABI | | | Microalbumin | | |
|---|---|---|---|---|---|---|---|---|---|---|---|---|---|---|---|---|---|---|---|
| | | N | BL | AB | N | BL | EL | N | BL | EL | N | BL | AB | N | AB | Abs | BL | Pres |
| Age 24 and Under | Male | 0 | 0 | 0 | 0 | 0 | 0 | 0 | 0 | 0 | 0 | 0 | 0 | 0 | 0 | 0 | 0 | 0 |
| | Female | 2 | 0 | 0 | 2 | 0 | 0 | 2 | 0 | 0 | 2 | 0 | 0 | 2 | 0 | 2 | 0 | 0 |
| Age 25-34 | Male | 9 | 5 | 1 | 8 | 1 | 6 | 11 | 3 | 1 | 7 | 3 | 5 | 15 | 0 | 14 | 0 | 1 |
| | Female | 7 | 3 | 0 | 9 | 0 | 1 | 8 | 1 | 1 | 9 | 1 | 0 | 10 | 0 | 6 | 2 | 2 |
| Age 35-44 | Male | 41 | 8 | 11 | 25 | 10 | 25 | 49 | 7 | 3 | 42 | 6 | 12 | 60 | 0 | 45 | 7 | 8 |
| | Female | 11 | 7 | 5 | 17 | 3 | 3 | 19 | 2 | 1 | 18 | 4 | 1 | 22 | 0 | 16 | 5 | 1 |
| Age 45-54 | Male | 34 | 10 | 12 | 22 | 11 | 23 | 29 | 14 | 10 | 32 | 15 | 9 | 55 | 1 | 42 | 7 | 7 |
| | Female | 18 | 5 | 10 | 18 | 8 | 8 | 20 | 7 | 6 | 23 | 8 | 3 | 34 | 0 | 24 | 8 | 2 |
| Age 55-64 | Male | 21 | 8 | 22 | 16 | 14 | 21 | 23 | 7 | 21 | 19 | 17 | 15 | 51 | 0 | 35 | 8 | 8 |
| | Female | 6 | 4 | 21 | 11 | 7 | 13 | 13 | 5 | 13 | 17 | 8 | 6 | 31 | 0 | 24 | 3 | 4 |
| Age 65-74 | Male | 10 | 4 | 10 | 9 | 3 | 12 | 7 | 5 | 11 | 6 | 10 | 8 | 24 | 0 | 17 | 3 | 4 |
| | Female | 2 | 7 | 10 | 7 | 4 | 8 | 6 | 3 | 9 | 4 | 9 | 6 | 18 | 1 | 15 | 2 | 2 |
| Age 75 and over | Male | 0 | 0 | 5 | 1 | 0 | 4 | 3 | 0 | 2 | 2 | 1 | 2 | 5 | 0 | 1 | 2 | 2 |
| | Female | 0 | 1 | 2 | 1 | 1 | 1 | 0 | 0 | 3 | 1 | 1 | 1 | 2 | 0 | 1 | 0 | 2 |
| | Untested | | | 1 | | | 0 | | | 6 | | | 0 | | 2 | | | 1 |

*Small artery elasticity assessed by pulse contour analysis. BP=blood pressure; ABI=ankle-brachial index; N=normal; BL=borderline; AB=abnormal; EL=elevated; Abs=absent; Pres=present

Figure 6

| Age Category | Gender | BNP | | | ECG | | | Cardiac Ultrasound | | |
|---|---|---|---|---|---|---|---|---|---|---|
| | | Normal | Borderline | High | Normal | Borderline | Abnormal | Normal | Borderline | Abnormal |
| Age 24 and Under | Male | 0 | 0 | 0 | 0 | 0 | 0 | 0 | 0 | 0 |
| | Female | 2 | 0 | 0 | 2 | 0 | 0 | 2 | 0 | 0 |
| Age 25-34 | Male | 15 | 0 | 0 | 13 | 2 | 0 | 9 | 3 | 2 |
| | Female | 9 | 2 | 1 | 9 | 1 | 0 | 6 | 2 | 2 |
| Age 35-44 | Male | 58 | 1 | 0 | 50 | 4 | 6 | 46 | 7 | 6 |
| | Female | 21 | 1 | 1 | 20 | 3 | 0 | 16 | 3 | 3 |
| Age 45-54 | Male | 53 | 2 | 1 | 31 | 13 | 12 | 45 | 7 | 2 |
| | Female | 30 | @ | 2 | 23 | 5 | 6 | 18 | 9 | 6 |
| Age 55-64 | Male | 47 | 3 | 1 | 40 | 4 | 7 | 40 | 3 | 4 |
| | Female | 29 | 1 | 1 | 26 | 0 | 5 | 21 | 5 | 4 |
| Age 65-74 | Male | 19 | 3 | 2 | 8 | 7 | 9 | 15 | 2 | 5 |
| | Female | 13 | 3 | 2 | 10 | 4 | 5 | 10 | 4 | 5 |
| Age 75 and over | Male | 4 | 0 | 1 | 1 | 1 | 1 | 1 | 2 | 0 |
| | Female | 1 | 1 | 1 | 3 | 0 | 0 | 4 | 1 | 0 |
| | Untested | | | | | | | | | 14 |

SCREENING FOR EARLY DETECTION OF CARDIOVASCULAR DISEASE IN ASYMPTOMATIC INDIVIDUALS

RELATED APPLICATIONS

This application is a continuation of U.S. patent application Ser. No. 10/372,001, filed Feb. 21, 2003, now abandoned which claims priority from U.S. Provisional Application No. 60/359,117, filed 21 Feb. 2002; which applications are incorporated by reference herein.

TECHNICAL FIELD OF THE INVENTION

The present invention relates generally to the field of medicine and more particularly, to diagnosis, monitoring, and treatment of disease.

BACKGROUND OF THE INVENTION

Most preventive efforts nationally have been devoted to risk factor modification in the asymptomatic population (primary prevention)[1,2] or intervention in individuals who have sustained cardiovascular morbid events (secondary prevention)[3-6]. Little attention has been directed to the early recognition of cardiovascular disease before organ involvement has occurred. Risk factor modification is aimed at preventing progression of disease but can have no benefit in individuals who do not have vascular or cardiac disease and are not at risk for a premature cardiovascular event. Furthermore, cardiovascular disease often exists and progresses in the absence of the traditional risk markers and its course can still be altered by intervention. Focusing on risk factor identification and management alone is doomed to insensitivity and non-specificity in achieving risk reduction, whereas focusing on individuals with advanced disease will not accomplish the desired goal of symptomatic disease prevention and health care cost reduction.

Risk markers such as age, blood pressure, cholesterol levels, blood sugar, homocysteine and inflammatory markers may correlate with the risk of cardiovascular events[7-10], much as the barometer may predict the likelihood of rain, but the first few raindrops are a far more sensitive and specific marker for raising the umbrella. Since potent interventions are now available to slow the progression of cardiovascular the need has increased for techniques that can identify the earliest markers for the disease rather than the risk. Such data might allow the application of a much more targeted approach to the prevention of first events in asymptomatic individuals.

A community testing and screening center was used to screen ostensibly healthy individuals in the Twin Cities community for detection of early markers for vascular and cardiac disease. A comprehensive array of non-invasive testing was developed using techniques that have either been established or advocated for early detection. In addition we undertook measurement of modifiable risk contributors that could serve to steer interventions in those with markers for disease.

BRIEF DESCRIPTION OF THE DRAWINGS

FIG. 1 is a tabular view of a range of values of arterial elasticity measurement.

FIG. 2 is a tabular view of a range of values of markers for cardiovascular disease.

FIG. 3 is a tabular view of laboratory test disease contributors.

FIG. 4 is a tabular view of patients by age and gender.

FIG. 5 is a tabular view of early vascular abnormalities.

FIG. 6 is a tabular view of early cardiac abnormalities.

DETAILED DESCRIPTION OF THE INVENTION

Methods

The history, physical examination and laboratory testing in the testing and screening center are carried out by a nurse practitioner with staff under her direction. Physician oversight includes chart and data review, report generation and, only when indicated, direct patient contact.

Screening consists of three phases: 1) risk category assignment; 2) early disease assessment; and 3) modifiable disease contributor assessment.

Risk Category Assignment

The extensiveness of the screening evaluation and its cost is based on risk category assignment. Certain tests are highly unlikely to be abnormal in low-risk individuals and their performance then cannot be justified on cost-benefit analysis. Individuals are therefore placed in low- or high-risk categories on the basis of information obtained on initial interview. The following are criteria for high-risk assignment:

1. Age. Men over 45 years of age and women over 55 years of age.
2. Family History. Individuals with one primary relative (parent or sibling) or two secondary relatives (grandparent, cousin, etc.) with cardiovascular disease or diabetes before the age of 65 in women and before 55 in men.
3. Personal History. Individuals who present with a history of an abnormal risk factor (blood pressure, cholesterol, blood sugar) or a previous presumed cardiovascular event.
4. Smokers.
5. Abnormal test results. In addition, individuals assigned to the low-risk category are reassigned to high-risk if any of their initial screening tests are determined to be abnormal.

Early Disease Assessment

The screening tests employed are designed to separately assess early markers for arterial and left ventricular disease.

Arterial Disease

Since endothelial dysfunction may be the earliest manifestation of arterial disease likely to progress to symptomatic atherosclerosis[14], the goal has been to assess early markers for endothelial and vascular dysfunction in an attempt to identify disease that has not become symptomatic. The following tests are employed:

1. Arterial elasticity. Pulse contour analysis allows separate assessment of the elasticity of the large conduit arteries and the small arteries that serve as sites of reflected waves in the circulation. A pulse wave analysis methodology developed at the University of Minnesota and now commercially marketed (Hypertension Diagnostics, Inc. Eagan, Minn.) is utilized. The methodology includes applying a piezoelectric transducer to a radial artery with on-line computer analysis of the pulse wave with a rapid printout of a cardiovascular profile that includes large artery elasticity ($C_1$) and small artery elasticity ($C_2$). Previous studies have validated the methodology, demonstrated the decline in $C_1$ and $C_2$ with aging, demonstrated abnormally low $C_2$ levels in patients with cardiovascular disease, and shown a correlation between risk factors for cardiovascular disease and a low $C_2$.[14]
2. Blood pressure at rest and during exercise. A standardized 3-minute treadmill exercise test at a 5 met workload is performed to monitor the rise in systolic blood pressure with exercise. A brisk rise has previously been shown to correlate with reduced arterial elasticity or compliance.[16]
3. Opticfundus photos. A digital camera (Canon, Greenville, S.C.) is used to image the optic fundus without the need for mydriasis. Fundus photos are analyzed for the A:V ratio and the presence of A:V crossing changes.
4. Microalbuminuria. A spot urine sample is analyzed for the albumin excretion per mg creatinine, a marker for small artery disease in the kidney.[17]
5. Ankle:brachial index (high-risk only). Systolic blood pressure is measured in the arm and leg by Doppler detection. A ratio of leg:arm systolic pressure below 0.90 is taken as evidence for lower extremity occlusive disease.[18]

Cardiac Disease:

Left ventricular disease precedes the onset of symptoms of cardiac dysfunction. Identification of early cardiac disease could allow intervention that may be effective in slowing progression.[11]
1. Electrocardiogram (high-risk only).
2. Left ventricular (LV) ultrasound. A hand-held portable echocardiographic unit (Sonosite, Bothell, Wash.) is used to screen the left ventricle for transverse diameter and wall thickness.
3. Plasma BNP concentration. Brain natriuretic peptide levels are a sensitive guide to left ventricular dysfunction.[19] BNP is assayed using an on-line platform that utilizes a drop of venous blood placed on a slide device for immediate analysis, manufactured by Biosite, of San Diego, Calif.
4. Pulmonary function. A forced expiratory volume measurement is performed using spirometry to identify cardiopulmonary disease.

Scoring System

Each of the tests employed is categorized as normal or abnormal. In some instances a borderline abnormal range is identified. The ranges assigned to each test are shown in FIGS. 1 and 2. An abnormal test contributes 2 points to an overall disease assessment score, a borderline test 1 point and a normal test 0. The overall score (range 0 to 20) provides a continuum from no disease to severe disease.

Modifiable Disease Contributors

When early disease is present, identification and aggressive treatment of modifiable factors that contribute to disease progression is mandatory. Such aggressive intervention may also be present in unusually high risk individuals (e.g., diabetics) even if early disease cannot be identified. When disease is not present, modest life-style interventions to lower the risk of disease development may still be prudent.
1. Blood pressure. Taken seated at rest.
2. Fasting lipid levels. Patients are instructed to come to the center fasting and blood is drawn for analysis of cholesterol, LDL, HDL and triglycerides.
3. Fasting blood sugar.
3. C-reactive protein. This inflammatory marker is associated with the risk of atherosclerotic events. Anti-inflammatory therapy may suppress the levels.
4. PAI-1. This platelet-aggregating factor may increase the risk of thrombotic events and may be suppressed by therapy.
5. Homocysteine, Elevated levels have been identified as a risk factor for atherosclerosis and may be suppressed by folic acid.

The results of some of these tests are divided into optimal, borderline and abnormal, with abnormal results clear targets for therapy and borderline tests optional targets, depending on the evidence for cardiovascular disease, as shown in FIG. 3.

Results

The demographics of 333 individuals tested in the Minneapolis/St. Paul, Minn., area whose results have been entered into the database are shown in FIG. 4. Although it was our initial concept that we would be screening healthy individuals to identify early, subclinical cardiovascular disease, it soon became apparent that many individuals with overt disease that was either unrecognized or inadequately treated were referring themselves for testing. Untreated hypertension and symptomatic coronary disease were the most frequent cardiovascular diagnoses. These could and should have been identified by primary care physicians.

Our testing procedures appeared effective in identifying pre-clinical vascular and cardiac disease that mandated initiation or change in medical therapy. The evidence for vascular disease is summarized in FIG. 5 and for cardiac disease in FIG. 6. Over 50% of the population exhibited one or more abnormalities, including elevated blood pressure in 125, abnormal small artery elasticity in 103, abnormal exercise blood pressure in 81, abnormal retinal vasculature in 68, microalbuminuria in 43, abnormal ECG in 51, abnormal left ventricular ultrasound in 39 and elevated BNP in 13. Including borderline abnormal tests would identify even a greater prevalence of early cardiovascular disease.

Abnormalities in the laboratory tests for disease contributors provide therapeutic opportunities specifically for those with detectable early disease. Recommendations for intervention are provided in a complete report sent both to the patient and the identified primary care physician. It must be understood that these test results are not necessarily representative of the general population. It is likely that individuals with strong family histories of cardiovascular disease and appropriate health concerns were more likely to refer themselves for testing.

Discussion

The traditional approach to reduction of risk for cardiovascular disease events has been two-fold: (1) screen the healthy population for "risk factors" and intervene with non-pharmacologic or pharmacologic approaches in those whose measurements are above a level defined as "normal"; and (2) intervene aggressively in those individuals who have suffered from a cardiovascular event with therapy aimed at "secondary prevention".

The fallacies of this approach from both a public health and individual patient standpoint are multiple. The "risk factors" measured, including blood pressure, cholesterol, blood sugar, inflammatory markers, etc., are neither sensitive nor specific for the atherosclerotic disease we are attempting to prevent. Furthermore, the so-called upper limit of normal of these measurements does not separate high from low risk. Indeed, each of these "risk factors" appears to display a continuous, nearly linear relationship between the level and the risk for cardiovascular events.[20] Thus, the risk for progression in individuals with demonstrable vascular disease is now recognized to be influenced even by "normal" levels of these risk factors. This insight has led to the recommendation of lipid lowering therapy in all patients who have sustained a coronary event, regardless of their cholesterol level, and the lowering of the threshold for blood pressure treatment in those with diabetes and vascular disease.

The fallacy of waiting for an event to occur before initiating aggressive secondary preventive therapy is obvious. Events usually occur in individuals with advanced disease. They are costly to the health care system and the well being of our patients. They portend a high risk for subsequent events and a shortened life expectancy.

The costs of future management of patients who have sustained an event are considerable. It is intuitive that interventions aimed at preventing progression in early, asymptomatic disease would yield a healthier population and a reduction in health care costs. Despite the clear advantages of this approach, little effort has been expended to develop comprehensive screening programs to detect early disease so that aggressive preventive efforts can be mounted.

Accordingly, there appears to be a need or demand for a community-oriented facility to undertake this effort. Among the first 333 individuals screened as referred to above more than 50% exhibited overt or asymptomatic disease in need of intervention or pharmacologic or therapy. Since all of these individuals were in a high socioeconomic group with health insurance and access to primary care physicians, it is clear that our health care system is not providing adequate management to identify and treat high risk individuals. Furthermore, because these individuals did not exhibit organ system symptoms that might have precipitated referral to a cardiovascular specialist, the burden of diagnosis and treatment must fall on the primary care physician.

According to one embodiment, a community testing center uses a specialized, nurse-practitioner managed screening program using state-of-the-art methodology not generally available in the primary care setting that empowers primary care physicians with data and recommendations that can be incorporated into their care of those individuals screened. The modest cost of the screening visit should be returned many times over by the prevention or delay in development of costly cardiovascular events.

The procedures utilized to screen for early vascular and cardiac disease in such a community center are, in one embodiment, selected based upon current published experience with many of the tests and physiologic concepts that led to the development of others. According to this philosophy, early disease rather than abnormal risk factors is the focus of therapeutic intervention. Indeed, the distinction between normal and abnormal values for risk factor assessment loses its meaning when early disease is present. In a treatment center of the present invention, treatment of even so-called normal levels of blood pressure and cholesterol are recommended. In the absence of evidence for vascular or cardiac disease, it is likely—although not yet proven—that events will not occur prematurely. Since management strategies in the present era at best delay further events, and since individuals without early disease may eventually develop disease and events in their later years, the economic burden of health care for cardiovascular events may merely be shifted to an older age. Thus, critical to the overall goal of reducing health care costs might be a societal decision regarding the upper age at which aggressive and expensive medical care is provided.

According to one example embodiment, the array of tests used to screen patients may change as experience grows and data accumulate. The scoring system described in herein represents an effort to quantitate the evidence for early vascular or cardiac disease. According to one example embodiment, it is a hypothesis that the higher the score the greater likelihood a cardiovascular event will occur. Interventions aimed at risk contributors should reduce the event rate, particularly when the risk contributors are significantly elevated. Thus the benefit of intervention may in part obscure the relationship between cardiovascular disease score and future event rate. According to yet another example embodiment, the aggressiveness of primary care physicians in following testing recommendations provided to them are another variable that is monitored.

In one other example embodiment, an abnormal test result is assigned a score of 2, a borderline abnormal test a score of 1, and a normal test a score of 0. Therefore, a maximum abnormal score is 20, and a perfectly normal score is zero. The tests administered are: (1) large artery elasticity, (2) small artery elasticity, (3) blood pressure at rest, (4) blood pressure during exercise, (5) retinal arteries (Optic fundus photo), (6) microalbuminuria requiring urine for microalbumin, (7) large artery disease (carotid ultrasound for wall thickness, previously ankle-brachial index), (8) electrocardiogram, (9) BNP blood assay, (10) left ventricular ultrasound. A total score of 6 or greater has been identified as indicative of significant disease in need of therapy.

While the invention has been particularly shown and described with reference to specified embodiments hereof, it will be understood by those skilled in the art that there are changes in form and details that may be made herein without departing from the spirit and scope of the invention.

REFERENCES

1. Grundy S M, Balady G J, Criqui M H, (complete authors). Primary prevention of coronary heart disease: guidance from FraminghaM. Circulation 1998; 97: 1876-87.
2. Downs J R, Clearfield M, Weis S, Whitney E, Shapiro D R, Beere P A, Langendorfer A, Stein E A, Kruyer W, Gotto A M Jr. Primary prevention of acute coronary events with lovastatin in men and women with average cholesterol levels: results of AFCAPS/TexCAPS. Air Force/Texas Coronary Atherosclerosis Prevention study. JAMA 1998; 279:1615-22.
3. Antiplatelet Trialists Collaboration. Secondary prevention of vascular disease by prolonged antiplatelet therapy. BMJ 1988; 296-331.
4. Gottlieb S S, McCarter R J, Vogel R A. Effect of beta-blockade on mortality among high risk and low-risk patients after myocardial infarction. N EngL J Med 1998; 339:489-97.
5. Scandinavian Simvastatin Survival Study Group. Randomised trial of cholesterol lowering in 4444 patients with coronary heart disease: the Scandinavian Survival Study (4S). Lancet 1994; 344:1383-9.
6. Long-term Intervention with Pravastatin in Ischemic Disease (LIPID) Study Group. Prevention of cardiovascular events and death with pravastatin in patients with coronary heart disease and a broad range of initial cholesterol levels. The Long-term Intervention with Pravastatin in Ischaemic Disease (LIPID) Study Group. N Engl J Med 1998; 339: 1349-57.
7 Clarke R, Daly L. Robinson K, Naughten E, Cahalane S, Fowler B, Graham I. Hyperhomocysteinemia: an independent risk factor for vascular disease. N Engl J Med 1991; 324:1149-55.
8. Stein II Rosenson R S. Lipoprotein Lp(a) excess and coronary heart disease. Arch Intern Med 1997; 157:1170-6.
9. Kannel W B. Blood pressure as a cardiovascular risk factor. JAMA 1996; 275:1571-76.
10. Ridker P M, Glynn R J, Hennekens C H. C-reactive protein adds to the predictive value of total and HDL cholesterol in determining risk of first myocardial infarction. Circulation 1998; 97:2007-11.

11. The SOLVD Investigators. Effect of enalapril on mortality and the development of heart failure in asymptomatic patients with reduced left ventricular ejection fractions. N Engl J Med 1992; 327:685-91.
12. Yusuf S, Sleight P, Pogue J, Bosch J, Davies R, Dagenais G. Effects of an angiotensin-converting-enzyme inhibitor, ramipril, on cardiovascular events in high-risk patients. The Heart Outcomes Prevention Evaluation Study Investigators. N Engl J Med 2000; 342:145-53.
13. Effect of metroprolol CR/XL in chronic heart failure: Metroprolol CR/XL. Randomised Intervention Trial in Congestive Heart Failure (MERIT-HF). Lancet 1999; 353: 2001-7.
14. Ross R. The pathogenesis of atherosclerosis: a perspective for the 1990's. Nature 1993; 362:801-9.
15. Cohn J N, Finkelstein S, McVeigh G, Morgan D, LeMay L, Robinson J, Mock J. Non-invasive pulse wave analysis for the detection of arterial vascular disease. Hypertension 1995; 26:503-8.
16. Lim P O, Shiels P, Anderson J, MacDonald T M. Dundee step test: a simple method of measuring the blood pressure response to exercise. J Human Hypertens 1999; 13:521-6.
17. Borch-Johnsen K, Feldt-Rasmussen B, Strandgaard S, Schroll M, Jensen J S. Urinary albumin excretion. An independent predictor of ischemic heart disease. Arteriosclerosis, Thrombosis & Vascular Bio 1999; 19:1992-7.
18. Hirsch A T, Criqui M B, Treat-Jacobson D, Regensteiner J G, Creager M A, Olin J W, Krook S H, Hunninghake D B, Comerota A J, Walsh M E, McDermott M M, Hiatt W R. Peripheral arterial disease detection, awareness, and treatment in primary care. JAMA 2001; 286:1317-24.
19. Maisel A S, Koon J, Krishnaswamy P, Kazenegra R, Clopton P, Gardetto N, Morrisey R, Garcia A, Chiu A, DeMaria A. Utility of B-natriuretic peptide as a rapid, point-of care test for screening patients undergoing echocardiography to determine left ventricular dysfunction. Am Heart J 2001; 141:367-74.
20. Cohn J N. Arteries, myocardium, blood pressure and cardiovascular risk: towards a revised definition of hypertension. Jrnl Hypertension 1998; 16:2117-24.

What is claimed is:
1. A method of assessing cardiovascular ailments in a human subject from a population of subjects seeking assessment of their cardiovascular health, and treating the subject to reverse or slow progression of the ailments, comprising:
 a) assessing early markers for arterial and left ventricular disease by performing a first set of tests on the subject, the first set of tests consisting of:
  1) measuring arterial elasticity using pulse contour analysis to provide separate assessment of the elasticity of the large conduit arteries and the small arteries that serve as sites of reflected waves in the circulation;
  2) measuring blood pressure at rest and during exercise;
  3) imaging the optic fundus of the subject and analyzing the image or images for the A:V ratio and the presence of A:V crossing changes;
  4) analyzing a urine sample from the subject for the albumin excretion creatinine;
  5) determining the wall thickness of at least one large artery;
 b) assessing early cardiac disease wherein a second set of tests are performed on at least some of the subjects from the population, the second set of tests consisting of:
  1) an electrocardiogram;
  2) a cardiac ultrasound to screen the left ventricle for transverse diameter and wall thickness;
  3) a test to determine plasma brain natriuretic peptide concentration levels as a marker for left ventricular dysfunction; and
  4) a pulmonary function test using forced expiratory volume measurements;
 c) individually scoring the early markers and cardiac disease assessments using a three point scoring system indicating normal, borderline, and abnormal results and using the individual scores to produce at least one overall score wherein the resultant overall score provides a risk assessment on a scale wherein one end of the scale indicates no treatment is needed and the other end represents the greatest evidence of disease in need of treatment and wherein a low score of the three point scoring system is classified as normal, an intermediate score of the three point scoring system is classified as borderline, and a high score of the three point scoring system is classified as abnormal; and
 d) intervening in the progression of cardiovascular illness in the subject by providing one or more treatments for the subject in order to reverse or slow the progression of actual or suspected cardiovascular ailments identified in the assessment.
2. A method according to claim 1 further including determining a global assessment of risk contributor interventional potential by performing one or more of the following tests:
 a) blood pressure taken seated at rests;
 b) fasting lipid levels;
 c) fasting blood sugar;
 d) C-reactive protein;
 e) PAI-1;
 f) homocysteine.
3. A method of assessing cardiovascular ailments in a human subject from a population of subjects seeking assessment of their cardiovascular health:
 a) assessing cardiovascular health by evaluating each of (i) the large arteries, (ii) the small arteries, and (iii) the heart of the human subject;
 b) wherein large artery assessment consists of:
  (i) sensing a pulse contour of the subject's arterial waveform and using the waveform to determine the C1 parameter to provide a measure of large artery elasticity;
  (ii) measuring the wall thickness of the carotid artery;
  (iii) using the C1 indication of large artery elasticity and the measure of wall thickness of the carotid artery to assess the health of the large arteries of the subject;
 c) wherein small artery assessment consists of:
  (i) sensing a pulse contour of the subject's arterial waveform and using the waveform to determine the C2 parameter to provide a measure of small artery elasticity;
  (ii) optically inspecting the retinal arteries of the subject and determining an indication of small artery health in the retina of the subject;
  (iii) analyzing a urine sample of the subject to test for microalbumin to determine an indication of small artery health in the kidney;
  (iii) using the C2 indication of small artery elasticity, the indication of small artery health in the retina and the indication of small artery health in the kidney to assess the health of the small arteries of the subject;
 d) wherein an assessment of the health of a combination of the small arteries and the large arteries of the subject consists of:
  (i) measuring the resting blood pressure of the subject;

(ii) measuring the blood pressure response to exercise of the subject;

(iii) using the measures of resting blood pressure and blood pressure response to exercise to assess the health of the combination of small arteries and large arteries of the subject;

e) wherein the assessment of the health of the subject's heart consists of:

(i) obtaining an electrocardiogram of the subject's heart and using the electrocardiogram to determine an indication of the health of the subject's heart;

(ii) imaging the left ventricle using ultrasound to determine an indication of the health of the left ventricle;

(iii) measuring Brain natriuretic peptide (BNP) levels in the subject's blood to detect left ventricular dysfunction;

(iv) using the indications of heart health determined from the electrocardiogram, ultrasound imaging of the left ventricle and BNP levels to assess the health of the subject's heart;

g) scoring the small artery assessment, the large artery assessment, the combination of small and large artery assessment, and the cardiac assessment and adding the scores to produce an overall score to provide at least one risk assessment score ranging from low to high, wherein the scoring uses a three point scoring system and wherein the assessments are scored on the three point scoring system based on predefined ranges for the assessments; and whereby there is provided a comprehensive assessment of the sites of cardiovascular disease that lead to heart attacks, strokes, heart failure, kidney failure, peripheral vascular disease, aneurysms, dementia or sudden death.

4. A method according to claim 3 wherein the assessments of the small arteries, large arteries and heart are performed in any order.

5. A method according to claim 3 further including prescribing for the subject one or more treatments to intervene in any cardiovascular disease identified using any one of the small artery, large artery, combination of small and large artery, or cardiac assessments.

6. A method according to claim 3 further including the subject intervening in any cardiovascular disease identified using any one of the small artery, large artery, combination of small and large artery, or cardiac assessments, wherein the subject takes one or more pharmaceuticals as part of the intervention or the subject modifies at least one behavior of the subject that impacts the health of the cardiovascular health of the subject.

* * * * *